United States Patent
Burdeniuc et al.

(10) Patent No.: US 6,245,932 B1
(45) Date of Patent: Jun. 12, 2001

(54) CYANOETHYLATION OF CYCLOALIPHATIC VICINAL PRIMARY DIAMINES

(75) Inventors: Juan Jesus Burdeniuc, Macungie; Gamina Ananda Vedage, Bethlehem, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/634,398

(22) Filed: Aug. 9, 2000

(51) Int. Cl.[7] .................. C07C 255/03; C07C 255/00
(52) U.S. Cl. ............................. 558/367; 558/431
(58) Field of Search ....................... 558/367, 431

(56) References Cited

U.S. PATENT DOCUMENTS

| | | | |
|---|---|---|---|
| 3,231,601 | 1/1966 | Peteril | 260/465 |
| 3,496,213 | 2/1970 | Ross | 260/465 |
| 4,153,567 | 5/1979 | Kluger | 252/51.5 A |
| 4,321,354 | 3/1982 | Kluger | 528/122 |

*Primary Examiner*—Joseph K. McKane
*Assistant Examiner*—Joseph Murray
(74) *Attorney, Agent, or Firm*—Russell L. Brewer

(57) ABSTRACT

A process for the cyanoethylation of substituted cycloaliphatic vicinal diamines which comprises reacting acrylonitrile and a diamine in the presence water as catalyst. Cyanoethylated methylcyclohexylamines are readily prepared in the presence of water.

8 Claims, No Drawings

CYANOETHYLATION OF CYCLOALIPHATIC VICINAL PRIMARY DIAMINES

BACKGROUND OF THE INVENTION

Processes for the reaction of primary and secondary amines with acrylonitrile to form corresponding cyanoethylamines are well-known. Products that result from the cyanoethylation of organic amines are of industrial importance because they have broad utility in a variety of applications. For example, cyanoethylated amines can be used as coupling components in the preparation of azo dyes for paper and synthetic fibers and so forth. Also, the pendant nitrile groups can be reduced to the amine and thereby generate polyfunctional amines for use as epoxy and isocyanate curatives.

In general, amines add to acrylonitrile more easily than many organic compounds, but the ease of the addition to amines varies considerably. For example, primary amines having two active hydrogen atoms can add one or two acrylonitrile molecules. Addition of the first acrylonitrile molecule to a primary amine may occur at relatively low temperature while addition of the second acrylonitrile molecule may require heating and the use of more rigorous conditions. Stereochemistry between primary or secondary amines and the complexity of the amine also affect the rate of addition of acrylonitrile to the amine.

The following patents represent processes for the cyanoethylation of primary and secondary amines:

U.S. Pat. No. 3,231,601 discloses the cyanoethylation of aromatic amines and points out that primary and secondary aromatic amines are more difficult to cyanoethylate than their aliphatic counterparts. Cyanoethylation of the aromatic amine is effected in good yield by carrying out the reaction in an aqueous medium, i.e. water as the sole solvent, and in the presence of salts of aromatic amines and strong acids as catalysts. The patentees also point out that primary amines are more easily reacted than secondary amines and that steric hindrance of the amine group can affect reactivity, e.g., o-toluidine is less reactive than p-toluidine. Examples of strong acids suited for the catalytic reaction include sulfuric, phosphoric, hydrochloric, p-toluene sulfonic, and trifluoroacetic.

U.S. Pat. No. 3,496,213 discloses the mono-N-cyanoethylation of aromatic amines by reacting the aromatic amine with acrylonitrile in the presence of zinc chloride carried in an aqueous reaction medium. In the process one mole of acrylonitrile is reacted with one mole of monoamine.

U.S. Pat. No. 4,153,567 discloses a process for producing additives for lubricants and fuel which are based on the reaction of the acrylonitrile and vicinal cyclohexanediamine followed by reaction with a heterocyclic imide. In the process, cyanoethylation is effected by reacting 1,2 diaminocyclohexane with acrylonitrile in the presence of an acid catalyst. One and two moles of acrylonitrile are reacted with the vicinal cyclohexylamine to give both the monocyanoethylated product, i.e., N-(2-cyanoethyl)-1,2-diaminocyclohexane and the dicyanoethylated product, i.e., N,N'-di-(2-cyanoethyl)-1,2-diaminocyclohexane. Acid catalysts that may be used include p-toluene-sulfonic acid and acetic acid. Following cyanoethylation the nitrile is reduced to the amine by a catalytic hydrogenation using Raney nickel or other transition metals as catalysts.

U.S. Pat. No. 4,321,354 discloses the production of cycloaliphatic polyamines, particularly the polyamine derived from 1,2-diaminocyclohexane. As in '567, 1,2diaminocyclohexane is reacted with one or two moles acrylonitrile respectively in the presence of an acetic acid catalyst to produce N,N'-di-(2-cyanoethyl)-1,2-diaminocyclohexane. The resultant cyanoethylated diaminocyclohexanes are reduced with hydrogen to form the polyfunctional amines.

BRIEF SUMMARY OF THE INVENTION

This invention relates to an improvement in a process for the cyanoethylation of vicinal cycloaliphatic diamines. The cyanoethylation of the vicinal cycloaliphatic primary amines is carried out in the presence of catalytically effective amount of water and in the substantial absence of inorganic or organic promoters such as acidic compounds. The cyanoethylated cycloaliphatic diamines are represented by this structure

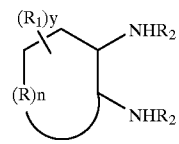

wherein R represents $CH_2$ and n is an integer from 1 to, 4 for forming a ring and preferably 1 or 2 thereby forming rings of 5 and 6 carbon atoms; $R_1$ represents H or alkylene groups or substituted alkylene groups having from 1 to 4 carbons atoms, hydroxyalkyl, carboxylic acid, amide, amino, etc., or a fused ring and y is an integer of from 1 to 2 when $R_1$ is other than hydrogen; and $R_2$ is H or and, further, at least one $R_2$ is represented by the formula: $—CH_2—CH_2—CN$.

Vicinal diaminocyclohexanes and derivatives are preferred as the substrate.

There are significant advantages associated with the cyanoethylation process and they include:

an ability to produce the N-(2-cyanoethyl) and N,N'-di-(2-cyanoethyl) vicinal cycloaliphatic diamines in high selectivity;

an ability to effect the cyanoethylation in the presence of water alone without the inclusion of inorganic or organic promoters, such as, acetic components or water-soluble amines which contribute to recovery problems;

an ability to effect the cyanoethylation in water which generates a water-insoluble product that is easily removed from the reaction medium; and, an ability to produce the N-(2-cyanoethyl) and N,N'-di-(2-cyanoethyl) vicinal cycloaliphatic diamines while obtaining excellent reaction rates.

In a preferred reaction, and used for purposes of illustration, ortho-methylcyclohexyldiamines ($H_6OTD$) is reacted with one or 2 moles acrylonitrile using water alone as the catalytic promoter. Reaction is limited to primary amine hydrogen even when molar concentrations of acrylonitrile are greater than 2:1 per mole of primary amine. The primary reaction products produced with water are designated A and B and set forth below. Analysis show that almost no compounds exhibiting secondary amine hydrogen reaction and represented by structures C and D are produced when water alone is used as the catalytic promoter.

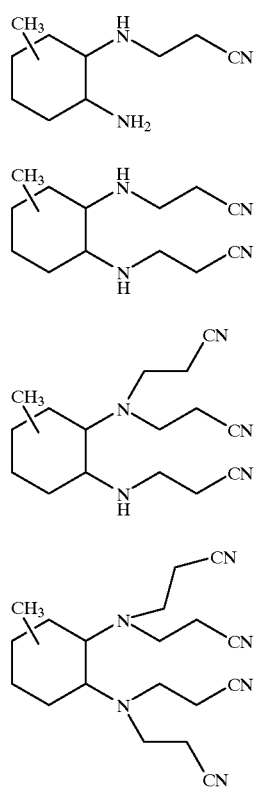

DETAILED DESCRIPTION OF THE INVENTION

Processes for the reaction of aliphatic amines and cycloaliphatic amines with crylonitrile to produce cyanoethylated amines are known. Although each hydrogen atom of a primary amine can react with one molar equivalent of acrylonitrile, the primary amine hydrogen atom is more reactive than is a secondary amine hydrogen atom. However, even though the secondary amine hydrogen atom is less reactive it is difficult to control the degree to which secondary amine hydrogen atom reacts in many catalytic processes. Often the reaction product is a mixture of cyanoethylated amines where some of the reaction product exhibits secondary amine reaction thereby resulting in the formation of compounds represented by products of the formulas C and D.

In the current process, one mole of acrylonitrile is reacted with one equivalent of primary amine hydrogen. Thus, in contrast to prior art procedures, water alone, when added in a catalytically effective amount, catalyzes the reaction of the primary amine hydrogen atoms with acrylonitrile to the substantial exclusion of reaction with secondary amine hydrogen atoms. Not only is the reaction selective, but also the rate of cyanoethylation is significantly greater that when no catalyst is employed. Although acidic components such as acetic acid have been used as catalytic promoters, the reaction is not as selective as when water is used as the sole catalyst. Further, the presence of acidic components often leads to contamination requiring greater purification efforts. A catalytic amount of water is used in the reaction. By a catalytic amount, it is meant that the amount of water is sufficient to noticeably increase the rate of reaction. Typically, molar concentrations of water per mole of cycloaliphatic diamine range from about 0.5 to 10:1 preferably from about 1 to 2:1. Excess quantities of water offer no significant advantages.

In the practice of the process described herein, cycloaliphatic vicinal diamines where there are from about 5 to 9 carbon atoms in the ring, preferably 5 or 6 are employed as the amine substrate, Examples of vicinal cycloaliphatic diamines commonly used in the cyanoethylation process are 1,2-diaminocyclohexane; 1-methyl-2,3-diaminocyclohexane and 1-methyl-3,4-diaminocyclohexane; t-butyl-diaminocyclohexane Other cyclbaliphatic diamines which can be used in the cyanoethylation reaction include: ethyidiaminocyclohexane, isopropyl diamino cyclohexane 1,2-diaminodehydronapthalenes, or o-diaminoperhydrophenthrenes, 1,2-diaminododecahydrofluroene, 1,2-diaminodecahydroquinoxalines, and o-diamino piperidines.

The temperature for effecting the reaction between acrylonitrile and the cycloaliphatic vicinal amines generally ranges from about 25 to 150° C. with preferred temperatures ranging from 60 to 80° C. Pressures for the reaction range from atmospheric to 60 psig. Atmospheric pressure for effecting the reaction is preferred.

EXAMPLE 1

Cyanoethylation Of $H_6$OTD With Acrylonitrile In A ~4:1 Ratio Of Acrylonitrile To Amine And In The Absence Of Water In a 250 ml three necked flask equipped with a magnetic stir bar, oil bath, reflux condenser and dropping funnel 32.66 g (0.25 mole) of dry and distilled $H_6$OTD (a mixture composed of 35% 2,3-diaminotoluene and 65% 3,4-diaminotoluene) was placed. The reaction vessel was heated up to 70° C. and 55.35 g of acrylonitrile (1.04 mole) was added dropwise. A mild exotherm occurred and the temperature was controlled during the addition so that it did not exceed 77° C. The addition of acrylonitrile was completed in about 20 minutes and the mixture was refuxed for 18 hours. Analysis by GCMS, Solid Probe-Mass Spectroscopy and Chemical Ionization Mass Spectroscopy with $NH_3$ and $ND_3$ of the resulting mixture showed: 36% of unreacted $H_6$OTD ($M^+$=128), 60% of the monocyanoethylated amine product previously described by formula A ($M^+$=181) and 1.23% of the dicyanoethylated amine product previously described by formula B ($M^+$=234).

These data show that cyanoethylation in the absence of a catalyst proceeds slowly in that only a 64% of $H_6$OTD reacted in 18 hours. Analysis of the reaction product also showed 60% conversion to the monocyanoethylated product and only a small amount of dicyanoethlylated product even at the high molar concentrations of acrylonitrile to primary amine hydrogen.

EXAMPLE 2

Cyanoethylation Of $H_6$OTD With Acrylonitrile In A ~2.5:1 Ratio Of Acrylonitrile To Amine And In The Absence Of Water The procedure of Example 1 was repeated essentially. In a 250 ml three necked flask equipped with a magnetic stir bar, oil bath, reflux condenser and dropping funnel, 30.90 g (0.24 mole) of $H_6$OTD (a mixture composed of 35% 2,3-diaminotoluene and 65% 3,4-diaminotoluene) was placed as received and the contents heated up to 70° C. 32 g of acrylonitrile (0.6 mole) were added dropwise so that the temperature did not exceed 77° C. The addition of acrylonitrile was completed in about 20 minutes. Samples were taken over a 24 hour period and the results are set forth in Table 1.

TABLE 1

| Time (hours) | Product A (% GC area) | Product B (% GC area) |
|---|---|---|
| 0.5 | 65.28 | 11.89 |
| 1.0 | 67.48 | 17.32 |
| 2.0 | 59.41 | 33.59 |
| 3.0 | 57.43 | 38.76 |
| 4.0 | 53.43 | 42.68 |
| 5.0 | 48.00 | 48.0 |
| 6.0 | 44.50 | 50.0 |
| 24 | 18.84 | 78.73 |

The results show that the dicyanoethylation reaction (Product B) proceeds slowly with little dicyanoethylation taking place in the first 6 hours under anhydrous conditions.

EXAMPLE 3

Cyanoethylation Of $H_6OTD$ With Acrylonitrile In A ~4:1 Ratio Of Acrylonitrile To Amine With Addition Of Water Water 4.0 g (0.22 mole), was added to the reaction mixture of Example 1 at 77° C. and a sample was taken after 10 minutes. Analysis showed that 56% of the mixture corresponded to the dicyanoethylated product represented by formula B. The results suggest that water catalyzed the reaction of acrylonitrile with unreacted methyl cyclohexylamine and with monocyanoethylated methyl cyclohexylamine in the reaction product.

EXAMPLE 4

Cyanoethylation Of $H_6OTD$ With Acrylonitrile In A ~2.5:1 Ratio Of Acrylonitrile To Amine And In The Presence Of Water In a 250 ml three necked flask equipped with a magnetic stir bar, oil bath, reflux condenser and dropping funnel 30.90 g (0.24 mole) of 1,2-diaminomethylcyclohexane and 7.7 g (0.42 mole) of water were placed. The reaction vessel was heated up to 70° C. and 32 g of acrylonitrile (0.6 mole) was added dropwise. An exotherm occurred and the temperature was controlled during the addition so that it did not exceed 77° C. The addition of acrylonitrile was completed in about 20 minutes. Once the addition was finished, a sample was analyzed by GCMS, Solid Probe-Mass Spectroscopy and Chemical Ionization Mass Spectroscopy with $NH_3$ and $ND_3$. The resulting mixture showed only the dicyanoethylated amine product B ($M^+$=234) (99.75%) yield.

This example shows the effect of adding a catalytically effective amount of water in that it initially enhanced the rate of reaction. Not only was the rate of reaction substantially greater than the rate of reaction in Example 2, as evidenced by the higher conversion, the selectivity to the dicyanoethylated product B was much higher than was obtained after a 24 hour reaction period.

EXAMPLE 5

Reaction Between $H_6OTD$ And Acrylonitrile In A 1/1 Molar Ratio And In The Presence Of Water In a 250 ml three necked flask equipped with a magnetic stir bar, oil bath, reflux condenser and dropping funnel, 31.29 g (0.24 mole) of 1,2-diaminomethylcyclohexane and 6.0 g (0.33 mole) of water were placed. The reaction vessel was heated up to 70° C. and 13 g of acrylonitrile (0.24 mole) was added dropwise with the temperature not surpassing 77° C. The addition of acrylonitrile was completed in about 15 minutes. Once the addition was finished, a sample was analyzed by GCMS, Solid Probe-Mass Spectroscopy and Chemical Ionization Mass Spectroscopy with $NH_3$ and $ND_3$. The resulting mixture showed mainly product of formula A ($M^+$=181) (85%) and product of formula B ($M^+$=234) (15%). Conversion was approximately 100%.

The results show excellent stoichiometric control of the reaction at a 1:1 mole ratio of acrylonitrile to amine and a ratio or ~1.4 moles water per mole of amine in that only a small amount of the dicyanoethylated product of formula B was produced. Conversion of amine to was excellent.

EXAMPLE 6

Cyanoethylation Of $H_6OTD$ With Acrylonitrile In The Absence Of Water Followed By The Addition Of Water In a 250 ml three necked flask equipped with a magnetic stir bar, oil bath, reflux condenser and dropping funnel, 32.66 g (0.25 mole) of 1,2-diaminomethylcyclohexanes were placed. The reaction vessel was heated to 70° C. and 55.35 g of acrylonitrile (1.04 mole) was added dropwise. A mild exotherm occurred and the temperature was controlled during the addition so that it did not exceed 77° C. The addition of acrylonitrile was completed in about 20 minutes. After that, the reaction mixture was heated under refux for 18 hours. Analysis by GCMS, Solid Probe-Mass Spectroscopy and Chemical Ionization Mass Spectroscopy with $NH_3$ and $ND_3$ of the resulting mixture showed 36% $H_6OTD$ ($M^+$=128) and 60% corresponded to the cyanoethylation of only one amine hydrogen as represented by the product of formula A (, $M^+$=181). Only a negligible amount (1.23%) corresponded to the product with both primary amine hydrogen atoms cyanoethylated product represented by formula B (, $M^+$=234).

Water 4.0 g (0.22 mole), was then added to this mixture at 77° C. and a sample was taken after 10 minutes for analysis and it showed that 56% of the mixture corresponded to B. Another sample was taken after two hours showing 70% B, 17.6% A and 12.1% $H_6OTD$. When water was added to the $H_6OTD$, followed by addition of acrylonitrile, then the reation proceeds to completion in 20 hours.

This experiment shows that the order in which the raw materials are mixed is important. When $H_6OTD$ is reacted with acrylonitrile first and then water is added to this mixture, as was done in Examples 2 and 3, the cyanoethylation of the vicinal cycloaliphatic amine does not proceed as fast when water is initially present as shown in Example 4.

What is claimed is:

1. In a process for the cyanoethylation of vicinal cycloaliphatic amines by contacting acrylonitrile with said vicinal cycloaliphatic amine under reaction conditions to produce a cyanoethylated diaminocyclohexane, the improvement which comprises;
effecting the reaction in the presence of a promoter consisting essentially of a catalytically effective amount of water.

2. The process of claim 1 wherein the vicinal cycloaliphatic amine is a diaminocyclohexane.

3. The process of claim 2 wherein the diaminocyclohexane is selected from the group consisting of 1,2- diaminocyclohexane; 1-methyl-2,3-diaminocyclohexane, 1-methyl-3,4-diaminocyclohexane; and t-butyl-2,3- and 3,4-diaminocyclohexane.

4. The process of claim 3 wherein the mole ratio of water to diaminocyclohexane is from to 0.5 to 10 moles water per mole of amine.

5. The process of claim 4 wherein the mole ratio of acrylonitrile to vicinal cycloaliphatic diamine is from to 1 to 4:1.

6. The process of claim 5 wherein the temperature reaction is from 60 to 80° C.

7. The process of claim 6 wherein the pressure is from atmospheric to 60 psig.

8. The process of claim 5 wherein the vicinal amine is 1-methyl-2,3-diaminocyclohexane or 1-methyl-3,4-diaminocyclohexane.

* * * * *